(12) United States Patent
Fjerdingstad

(10) Patent No.: US 7,082,848 B2
(45) Date of Patent: Aug. 1, 2006

(54) METHOD OF TRANSFERRING A REPRESENTATIVE FLUID SAMPLE FROM A PRESSURIZED SOURCE INTO A SAMPLE BOTTLE

(76) Inventor: Sølve Fjerdingstad, Plogsvingen 10, N-1410 Kolbotn (NO)

( * ) Notice: Subject to any disclaimer, the term of this patent is extended or adjusted under 35 U.S.C. 154(b) by 0 days.

(21) Appl. No.: 11/080,929

(22) Filed: Mar. 16, 2005

(65) Prior Publication Data

US 2005/0183519 A1   Aug. 25, 2005

Related U.S. Application Data

(63) Continuation of application No. PCT/NO2003/000317, filed on Sep. 16, 2003.

(30) Foreign Application Priority Data

Sep. 16, 2002   (NO) .................................. 20024415

(51) Int. Cl.
*G01N 1/10* (2006.01)
(52) U.S. Cl. ............................... 73/863.85; 73/863.41; 73/863.81
(58) Field of Classification Search ............. 73/863.81, 73/863.85, 863.82, 863.41
See application file for complete search history.

(56) References Cited

U.S. PATENT DOCUMENTS

| | | | | |
|---|---|---|---|---|
| 3,954,012 A | * | 5/1976 | Christen et al. | 73/864.21 |
| 4,478,095 A | * | 10/1984 | Bradley et al. | 73/864.21 |
| 4,669,321 A | * | 6/1987 | Meyer | 73/863.85 |
| 5,012,845 A | | 5/1991 | Averette | |
| 5,370,005 A | * | 12/1994 | Fjerdingstad | 73/863.71 |
| 5,432,098 A | | 7/1995 | Wilks | |
| 5,483,843 A | * | 1/1996 | Miller et al. | 73/864.23 |
| 5,578,495 A | | 11/1996 | Wilks | |
| 5,604,320 A | * | 2/1997 | Boyd | 73/863.86 |
| 6,395,560 B1 | * | 5/2002 | Markelov | 463/181 |
| 2002/0006360 A1 | | 1/2002 | Neal et al. | |

* cited by examiner

*Primary Examiner*—Hezron Williams
*Assistant Examiner*—Nashmiya Fayyaz
(74) *Attorney, Agent, or Firm*—Wenderoth, Lind & Ponack, L.L.P.

(57) ABSTRACT

An injection needle particularly intended for transferring a representative fluid sample into a sample bottle (1) is closed by a membrane (2) made from a rubber elastic material. The needle has a tubular inner wall (6) having a needle point (8), and a tubular outer wall (10) concentrically surrounding and radially spaced from the inner wall (6) at least along a portion thereof distant from the needle point (8) and, at its end facing the needle point, having a conically tapering portion (12) sealingly engaging the inner wall (6). The outer wall (10) is provided with at least two apertures (14, 16) spaced longitudinally of the needle. When using the injection needle for the above purpose, fluid is injected into the sample bottle (1) from a fluid source of interest by inserting the injection needle into the sample bottle through the membrane to a level at which the penetrated portion of the membrane (2) sealingly engages the outer wall (10) of the needle between the spaced apertures (14, 16) in the outer wall, such that initially some of the fluid that is injected into the bottle is allowed to flow into the annulus between the inner and outer walls of the needle (4), through the aperture (14) of the outer wall at the inside of the membrane, and hence out through the aperture (16) of the outer wall to the outside of the membrane.

2 Claims, 1 Drawing Sheet

METHOD OF TRANSFERRING A REPRESENTATIVE FLUID SAMPLE FROM A PRESSURIZED SOURCE INTO A SAMPLE BOTTLE

REFERENCE TO RELATED APPLICATION

This is a continuation of PCT/NO2003/000317, filed Sep. 16, 2003.

FIELD OF THE INVENTION

The invention relates to a method for transferring a representative pressurized fluid sample into a sample bottle. By the phrase "representative fluid sample" is here meant a sample in which the fluid is substantially identical to the fluid from which the sample is taken, i.e. in which the fluid has not been contaminated or otherwise changed or influenced by the exterior during the sampling operation itself.

BACKGROUND OF THE INVENTION

EP patent 548 187 discloses a sampling method and assembly for taking representative samples from pressurized fluid systems, particularly hydraulic or lubricating oil systems. In some cases, however, the patented sampler may not be able to secure a completely representative fluid sample. In particular, this is so in cases where it is desirable to analyse the gas contents of a fluid. An example is samples from insulation oil in a transformer which, when it is old and worn, loses its insulation properties, resulting in a danger of explosion caused by sparks that may occur owing to the insulation defects. Such sparks result in the formation of free acetylene and hydrogen which could be detected in a gas chromatograph. The latter gas, in particular, appears in very low concentrations and is very elusive. Thus, a prerequisite for obtaining a correct result from an analysis that accurately indicates the amount of hydrogen in the sample is that no gas escapes during the sampling operation. Similarly, when sampling fluids included in processes of the food industry or pharmaceutic or medical processes, it is most important that sterile samples are not contaminated by micro organisms. In such cases the fluid sample would normally be tapped directly into a sampling bottle which is then sealed by a fluid-tight membrane. Also in this case there is the danger that the sample fluid be contaminated when transferred to the sample bottle.

SUMMARY OF THE INVENTION

The invention according to the present application provides a simple and effective solution of the above problem. The solution involves transferring the fluid sample from the pressurized fluid system into an empty, possibly sterilized sample bottle, which has been pre-sealed by a high elasticity membrane or diaphragm, by injection via a double-walled needle penetrating the membrane.

BRIEF DESCRIPTION OF THE DRAWINGS

The invention will now be described in detail, with reference to the accompanying, partly schematic drawings, in which.

DETAILED DESCRIPTION OF THE PREFERRED EMBODIMENT

Figure 1:
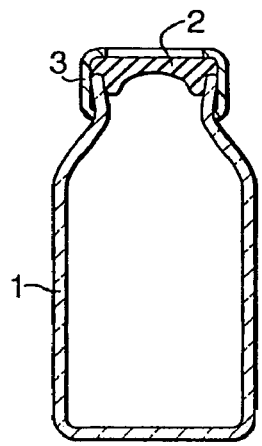
FIG. 1 illustrates a traditional membrane-sealed sample bottle.

A sample bottle 1 illustrated in FIG. 1 is of the usual type for "hermetically" sealed storing of a fluid sample, such as those used within medicine and pharmacies. It would normally be made from glass, with a relatively wide mouth which is closed by a closure member in the form of a relatively thin-walled plug or "membrane" made of a rubber-elastic material (elastomer). The membrane 2 is retained in position over the bottle mouth in a wellknown manner, such as by a circumferential plastic seal 3, for example.

Figure 2:
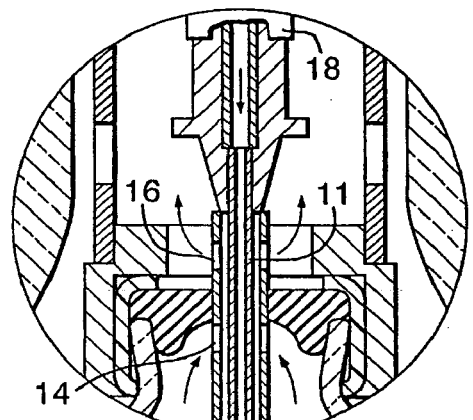
FIGS. 2 and 3 illustrate an injection needle according to the invention in two stages during sampling.
Figure 3:
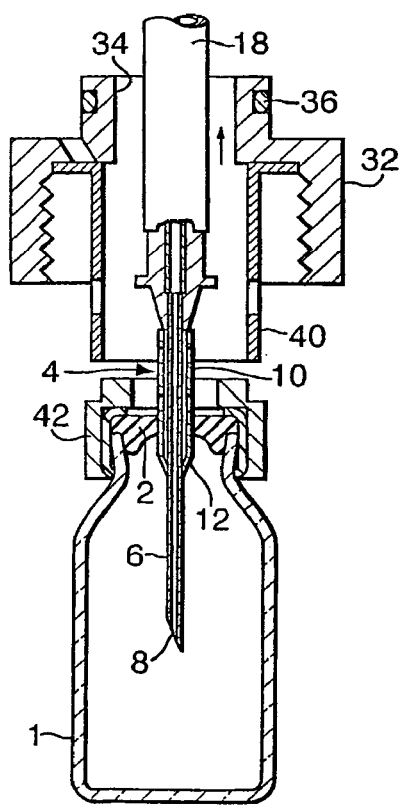
Figure 3:
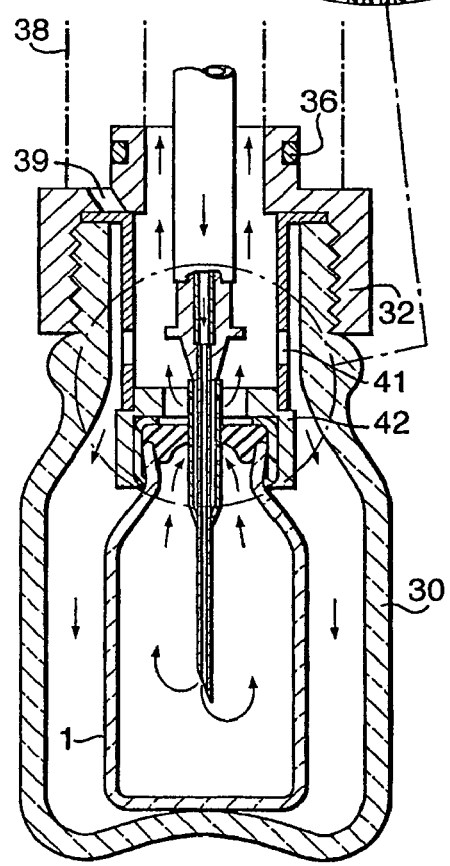

The essential aspect of the invention is the use of a hollow, double-walled, perforated needle 4, as illustrated in FIGS. 2 and 3, for injecting a fluid sample into the sample bottle 1. The needle 4 comprises a tubular inner wall 6 having a bevelled needle point 8, generally similar to that of an ordinary injection needle. The inner wall 6, at least along an upper portion thereof (i.e. spaced from the needle point 8), is surrounded by a tubular outer wall 10 radially spaced from the inner wall 6 to form an annulus 11. The outer wall 10, at the lower end thereof (i.e. the end proximate needle point 8), has a conically tapering portion 12 sealingly closing about inner wall 6. Further, as an essential feature of the invention, the outer wall 10 is provided with apertures 14 and 16, respectively, at two longitudinally spaced levels.

One example of using the needle 4 according to the invention, for injecting a fully representative fluid sample into a closed sample bottle as discussed above, is as follows.

The fluid is part of a pressurized circulating fluid system, e.g. of the same kind as described in EP 548 187. The following example is based on use of the needle according to the invention in connection with a circulating pressurized fluid system of the latter kind.

In FIG. 2 the sample bottle 1 is placed in a pressure vessel 30, which in this example is bottle-shaped with a threaded top portion mating with a correspondingly threaded cap 32 having a central opening 34 and circumferential seal ring 36 for sealingly connecting the bottle cap 32 to the pressurized fluid system of interest, such as via a tube 38 as indicated with broken lines in FIG. 2, and closing and shut-off valves and pressure release valves (not shown) as necessary. Centrally and directly below the cap opening 34 there is a sleeve 40, the lower end of which slidingly fits onto an upper portion of an adapter 42 at the top of the sample bottle 1, thereby retaining the latter positioned in pressure vessel 30 during the sampling operation. The side wall of sleeve 40 has apertures 41 permitting free fluid through-flow.

Needle 4 is connected to a valved fluid supply pipe 18 extending down from the fluid source of interest with its lower end portion sealingly surrounding an upper end portion of the inner wall 6 of the needle 4, while the upper end of the outer wall 10 is preferably sealingly engaging the end face of the supply pipe 18. The supply pipe 18 with needle 4 extends centrally down through the opening 34 in the pressure bottle cap 32 which, together with supply pipe 18 and tube 38, would preferably be stationarily installed, for example fixedly connected to the fluid source armature (not shown).

In FIG. 2 the needle 4 has penetrated the elastic membrane 2 of the sample bottle 1 to a level at which the edge or peripheral portion surrounding the hole in the penetrated membrane sealingly engages the unbroken portion of the needle outer wall 10 between the upper and lower apertures 16, 14 therein. In this position of the needle 4 fluid will flow, as indicated with arrows in FIG. 2, from supply pipe 18 in through the central bore of the needle tubular inner wall 6 and out into sample bottle 1 at the needle point 8, thence into the annulus 11 through the lower aperture 14 in outer wall 10 below membrane 2, out again from the annulus through the upper aperture 16 above the membrane and into the pressure bottle 30 through the apertures 41, and thence back into the fluid source via tube 38.

When the fluid flow through the sample bottle has continued for a certain period of time, insuring that the fluid present in the sample bottle, which could be a liquid, gas or both, is fully representative of the fluid of the fluid source, the supply of fluid is interrupted, the pressure in the pressurized vessel 30 is relieved and the vessel removed from the cap 32, leaving the sample bottle containing the fluid sample of interest freely suspended in the sleeve 40. When the sample bottle 1 is now pulled away from sleeve 40 down to the position shown in FIG. 3, where also the lower aperture 14 in the needle outer wall is above membrane 2, the fluid path through the needle annulus 11 is closed. Upon continued pulling down of the sample bottle until needle 4 lets go of membrane 2, the hole made by the needle when penetrating the membrane will be completely closed owing to the rubber elastic nature of the membrane, so that neither gas nor liquid will escape from the bottle. In order to provide an additional safe guarding of the tightness of the membrane hole, a piece of tape could be placed across the hole.

In FIG. 2 the upper aperture 16 in the needle outer wall 10 is shown as a distinct perforation in the outer wall. Instead, the upper aperture 16 could be provided by an opening or mouth at the upper end of the tubular outer wall 10, which in that case would not sealingly engage the end face of supply pipe 18.

As noted above, the needle 4 would normally be stationary and penetrate membrane 2 by lifting the sample bottle onto the needle from below, but the arrangement may of course be vice versa, i.e. keeping the sample bottle stationary while moving the needle from above down through the membrane.

The vessel 30 with cap 32 does not necessarily have to be formed with a pressure-resistant material, even if the pressure of the fluid source is relatively high. Instead, the vessel 30 with cap and sample bottle 1 therein could be placed in the pressure chamber 2 of a sampler according to EP 548 187. The bottle cap 32 would then substantially correspond to the bottle cap 24 of the sampler and dimensioned to replace the latter cap in a such sampler, and be provided with a fluid path into the pressure chamber as indicated at 39. The upper part 6 of pressure chamber 2 in the sampler would then replace tube 38 in the above described example, and in other respects be adapted to the supply pipe 18 with needle 4.

The invention claimed is:

1. A method for transferring a representative fluid sample from a pressurized fluid source into a sample bottle, the sample bottle having an opening closed by membrane made from a rubber-elastic material, said method comprising:

placing the closed sample bottle into a pressure vessel having a cap with a central opening that communicates with the pressurized fluid source via a tube;

connecting an upper end of a tubular inner wall of an injection needle, the tubular inner wall having a needle point, to the pressurized fluid source; and inserting the needle into the sample bottle through the membrane to a level at which the membrane sealingly engages a tubular outer wall of the needle, which tubular outer wall concentrically surrounds and is radially spaced from the inner wall at least along a portion of the inner wall distant from the needle point, the membrane sealingly engaging the outer wall between longitudinally spaced apertures in the outer wall such that initially some of the fluid injected from the pressurized fluid source is allowed to flow into an annulus between the inner wall and the outer wall of the needle through one of the spaced apertures of the outer wall inside of the sample bottle on one side of the membrane, then out through another of the spaced apertures of the outer wall outside of the sample bottle on the other side of the membrane, and then back to the fluid source through the tube.

2. A method for transferring a representative fluid sample from a pressurized fluid source into a sample bottle, the sample bottle having an opening closed by a membrane made from a rubber-elastic material, using an injection needle comprising a tubular inner wall having a needle point and a tubular outer wall that concentrically surrounds and is radially spaced from the inner wall at least along a portion of the inner wall distant from the needle point, has a conically tapering portion engaging the inner wall at an end of the outer wall facing the needle point, and has longitudinally spaced apertures, said method comprising:

placing the closed sample bottle into a pressure vessel having a cap with a central opening that communicates with the pressurized fluid source via a tube;

connecting an upper end of the inner wall of the needle to the pressurized fluid source; and inserting the needle into the sample bottle through the membrane to a level at which a penetrated portion of the membrane sealingly engages the outer wall of the needle between the spaced apertures in the outer wall such that initially some of the fluid injected from the pressurized fluid source is allowed to flow into an annulus between the inner wall and the outer wall of the needle through one of the spaced apertures of the outer wall inside of the sample bottle on one side of the membrane, then out through another of the spaced apertures of the outer wall outside of the sample bottle on the other side of the membrane, and then back to the fluid source through the tube.

* * * * *